United States Patent [19]

Rodon

[11] E Re. 31,397

[45] Reissued Sep. 27, 1983

[54] ORAL COMPOSITIONS

[75] Inventor: Maria Rodon, Raleigh, N.C.

[73] Assignee: Beecham Inc., Clifton, N.J.

[21] Appl. No.: 223,312

[22] Filed: Nov. 9, 1981

Related U.S. Patent Documents

Reissue of:

[64] Patent No.: 4,183,916
Issued: Jan. 15, 1980
Appl. No.: 892,276
Filed: Mar. 31, 1978

[51] Int. Cl.[3] ..... A61K 7/16; A61K 7/22

[52] U.S. Cl. ..... 424/54; 424/49; 424/55

[58] Field of Search ..... 424/48–58

[56] References Cited

U.S. PATENT DOCUMENTS

| | | | |
|---|---|---|---|
| 1,275,275 | 8/1918 | Lovinson | 424/55 |
| 3,124,506 | 3/1964 | Holman | 424/55 |
| 3,151,028 | 9/1964 | Hay et al. | 424/55 |
| 3,887,701 | 6/1975 | Nachtigal | 424/54 |
| 3,925,543 | 12/1975 | Donohue | 424/52 |
| 3,934,002 | 1/1976 | Haefele | 424/54 |
| 3,937,805 | 2/1976 | Harrison | 424/52 |
| 3,937,807 | 2/1976 | Haefele | 424/52 |
| 4,001,393 | 1/1977 | L'Orange | 424/49 |
| 4,051,234 | 9/1977 | Gieske et al. | 424/52 |
| 4,067,962 | 1/1978 | Juneja | 424/52 |
| 4,183,916 | 1/1980 | Rodon | 424/54 |

FOREIGN PATENT DOCUMENTS 1365030 8/1974 United Kingdom .

*Primary Examiner*—Shep K. Rose
*Attorney, Agent, or Firm*—Jacobs & Jacobs

[57] ABSTRACT

Oral compositions useful for controlling dental plaque and gingivitis and for preventing caries are produced comprising a cationic antimicrobial agent and an anti-stain agent which reduces the staining effect of the cationic antimicrobial.

14 Claims, No Drawings

ORAL COMPOSITIONS

Matter enclosed in heavy brackets [ ] appears in the original patent but forms no part of this reissue specification; matter printed in italics indicates the additions made by reissue.

The present invention is concerned with oral compositions useful for controlling dental plaque and gingivitis and for preventing caries. The active agent is a cationic antimicrobial agent, such as bisbiguanides or quaternary ammonium compounds, which agents are known in the art to be useful for such purposes. It is also known in the art that cationic antimicrobial agents such as bisbiguanides and quaternary ammonium compounds have the disadvantages of staining teeth. The present invention provides an oral composition utilizing bisbiguanides or quaternary ammonium compounds together with an anti-stain agent which reduces the staining effect of the bisbiguanide or quaternary ammonium compound to a level which is cosmetically acceptable.

It is known in the art that bisbiguanides inhibit the formation of plaque and caries (see U.S. Pat. No. 1,365,030) and that anti-calculus agents may be combined therewith to inhibit the tendency of the bisbiguanides to stain the oral surfaces (see U.S. Pat. No. 3,934,002). Among the anti-calculus agents disclosed in U.S.Pat. No. 3,934,002 are quaternary ammonium compounds, zinc phenolsulfonate, hydroxyquinoline, citric acid, lactic acid and pharmaceutically acceptable salts thereof.

The present invention is based on the surprising discovery that malic acid markedly inhibits the staining on oral surfaces of the bisbiguanide or quaternary ammonium active agent of the instant compositions.

More particularly, the present invention comprises an oral composition useful for controlling dental plaque and gingivitis and for preventing caries which comprises an effective amount of a bisbiguanide or quaternary ammonium compound which is capable of controlling dental plaque and gingivitis and preventing caries and a stain-inhibiting amount of malic acid.

According to one embodiment of the present invention the antimicrobial agent is a bisbiguanide.

According to another embodiment of the present invention the antimicrobial agent is a quaternary ammonium compound.

According to another embodiment of the present invention the amount of antimicrobial agent is from 0.01% to about 1.0% w/w based on the total weight of ingredients or w/v when in liquid form.

According to another embodiment of the present invention the amount of malic acid is from 0.1% to 10.0% w/w or w/v, especially from 0.1% to 1.0%.

According to another embodiment of the present invention the pH of the composition is from about 5.0 to about 8.0.

According to another embodiment of the present invention the bisbiguanide is 1,6-bis(2-ethylhexyldiguanido hexane)dihydrochloride [alexidine dihydrochloride]; 1,6-bis(2-ethylhexyl diguanido hexane)dihydrofluoride; 1,6-bis(2-ethylhexyl diguanido octane)dihydrochloride; 1,6-bis(2-ethylhexyl diguanido nonane)dihydrochloride; 1,6-bis(2-ethylhexyl diguanido dodecane)dihydrochloride; or 1,6-di(4-chlorophenyl diguanido hexane)dihydrochloride or the diacetate or digluconate salt thereof. Alexidine dihydrochloride is especially preferred.

According to another embodiment of the present invention the quaternary ammonium compound is dodecyl dimethyl(2-phenoxyethyl)-ammonium; benzyldimethyl(2-)2-(p-1,3,3-tetramethyl butyl phenoxy)ethoxyl)ethyl)ammonium; p-bromobenzyldimethyl-γ-(2'-isopropyl, 4'-chloro, 5'-methyl phenoxy)propyl ammonium; 1-hexadecyl-pyridinium salt; acylchloaminoformylmethyl pyridinium chloride-iodide complex; 1-alkyl-4-aminoquinaldinium salt; decamethylene bis(4-aminoquinaldinum chloride or hexadecamethylene bis(isoquinolinium chloride).

The usual flavoring agents, binders, sudsing agents, humectants, alcohols, fragrances, abrasives and excipients known in the art can be added to the compositions of the present invention.

When the oral composition of the present invention is in the form of a mouthwash, oral rinse or gargle, the composition is brought into contact with the oral cavity and then expectorated. A dose of 15 to 20 ml. for adults and about 10 ml. for children is generally sufficient when used on a daily basis.

When the instant composition is in the form of a dentifrice, such as a paste, powder, concentrate, solution or gel for direct application to the teeth, it can be used in the normal manner in which a toothpaste is used. When the oral composition of the present invention is in a concentrate for use with mechanical irrigation devices such as a water jet or "water pik" type device, approximately 10 to 15 ml. should be sprayed into the mouth and circulated in the oral cavity and then be expectorated. When the present composition is in the form of a breath freshener, either pump spray or aerosol type, approximately 10 to 15 ml. should be sprayed into the mouth, circulated therethrough and expectorated. When the composition of the present invention is in the form of a troche or a lozenge, it should be allowed to dissolve in the mouth and then be expectorated.

The following nonlimitative example more particularly illustrates the present invention.

| Ingredients | Percent W/V |
|---|---|
| Alexidine Dihydrochloride | 0.035 |
| Alcohol USP | 15.0 |
| Glycerin USP | 10.0 |
| Flavor | 0.4 |
| Sodium Saccharin | 0.02 |
| Malic Acid | 0.382 |
| Buffering Agent to pH 5.0–8.0 | |
| Water USP | q.s. |

The mouth-rinse is used in 15 ml. doses for adults to rinse the mouth and then is expectorated. For children in the 6 to 12 year old range, 10 ml. is the recommended mouth-rinsing dose.

What is claimed is:

[1. An oral composition useful for controlling dental plaque and gingivitis and for preventing caries which comprises from 0.1% to about 1.0% w/w or w/v of a cationic antimicrobial agent otherwise tending to stain teeth, and useful for controlling dental plaque and gingivitis and for preventing caries selected from the group consisting of a bisbiguanide or quaternary ammonium compound and from 0.01% to 10.0% w/w or w/v of malic acid effective to inhibit said teeth staining, in combination with a pharmaceutically acceptable carrier.]

[2. A composition according to claim 1 wherein the amount of malic acid is from 0.1% to 1.0% w/w or w/v.]

[3. A composition according to claim 1 wherein the pH of the composition is from about 5.0 to about 8.0.]

[4. A composition according to claim 1 wherein the bisbiguanide is 1,6-bis(2-ethylhexyl diguanido hexane)-dihydrochloride; 1,6-bis(2-ethylhexyl diguanido hexane)dihydrofluoride; 1,6-bis(2-ethylhexyl diguanido octane)dihydrochloride; 1,6-bis(2-ethylhexyl diguanido nonane)dihydrochloride; 1,6-bis(2-ethylhexyl diguanido dodecane)dihydrochloride; or 1,6-di(4-chlorophenyl diguanido hexane)dihydrochloride or the diacetate or digluconate salt thereof.]

[5. A composition according to claim 1 wherein the quaternary ammonium compound is dodecyl dimethyl(2-phenoxyethyl)-ammonium; benzyldimethyl(2-)2-(p-1,3,3-tetramethyl butyl phenoxy)ethoxyl)ethyl)ammonium; p-bromobenzyl-dimethyl-γ-(2'-isopropyl, 4'-chloro, 5'-methyl phenoxy)-propyl ammonium; 1-hexadecyl-pyridinium salt; acylcholaminoformyl-methyl pyridinium chloride-iodide complex; 1-alkyl-4-aminoquinaldinium salt; decamethylene bis(4-aminoquinaldinum chloride) or hexadecamethylene bis(isoquinolinium chloride).]

[6. A composition according to claim 1 wherein the antimicrobial agent is alexidine dihydrochloride.]

[7. A composition according to claim 1 in mouthwash form.]

[8. A composition according to claim 1 in oral rinse form.]

[9. A composition according to claim 1 in dentifrice form.]

[10. A composition according to claim 1 in toothpowder form.]

[11. A composition according to claim 1 in oral solution form.]

[12. A composition according to claim 1 in gel form.]

[13. A composition according to claim 1 in a form suitable for dispensing through a water jet.]

[14. A composition according to claim 1 in a breath freshener form.]

[15. A composition according to claim 1 in an aerosol form.]

[16. A composition according to claim 1 in a gargle form.]

[17. A composition according to claim 1 in the form of a troche.]

[18. A composition according to claim 1 in lozenge form.]

[19. A composition according to claim 1 which comprises 0.035% w/v alexidine dihydrochloride, 0.382% w/v malic acid and purified water as the pharmaceutically acceptable carrier, the pH of the composition being between 5.0 and 8.0.]

[20. A composition according to claim 1 which comprises 0.035% w/v alexidine dihydrochloride, 15.0% w/v alcohol USP. 10.0% w/v glycerin USP, 0.04% w/v flavoring agent, 0.02% w/v sodium saccharin, 0.382% w/v malic acid, sufficient buffering agent to maintain the pH of the composition between 5.0 and 8.0 and purified water UPS, q.s.]

*21. In the art of inhibiting teeth staining caused by a cationic anti-microbial agent which is useful for controlling dental plaque and gingivitis and for preventing caries selected from the group consisting of a bisbiguanide or a quaternary ammonium compound, said cationic anti-microbial agent being utilized in an amount of from 0.01% to about 1.0% w/w or w/v, the improvement which consists essentially of the step of orally utilizing together with said cationic anti-microbial agent, an amount of malic acid effective to inhibit teeth staining caused by the otherwise useful cationic anti-microbial agent, said amount of malic acid being from 0.01% to 10.0% w/w or w/v.*

*22. The improvement according to claim 21 wherein the amount of malic acid is from 0.1% to 1.0% w/w or w/v.*

*23. The improvement according to claim 21 wherein the cationic anti-microbial agent and the malic acid are utilized in mouthwash form.*

*24. The improvement according to claim 21 wherein the cationic anti-microbial agent and the malic acid are utilized in oral rinse form.*

*25. The improvement according to claim 21 wherein the cationic anti-microbial agent and the malic acid are utilized in dentifrice form.*

*26. The improvement according to claim 21 wherein the cationic anti-microbial agent and the malic acid are utilized in toothpowder form.*

*27. The improvement according to claim 21 wherein the cationic anti-microbial agent and the malic acid are utilized in oral solution form.*

*28. The improvement according to claim 21 wherein the cationic anti-microbial agent and the malic acid are utilized in gel form.*

*29. The improvement according to claim 21 wherein the cationic anti-microbial agent and the malic acid are utilized in a form suitable for dispensing through a water jet.*

*30. The improvement according to claim 21 wherein the cationic anti-microbial agent and the malic acid are utilized in a breath freshener form.*

*31. The improvement according to claim 21 wherein the cationic anti-microbial agent and the malic acid are utilized in an aerosol form.*

*32. The improvement according to claim 21 wherein the cationic anti-microbial agent and the malic acid are utilized in a gargle form.*

*33. The improvement according to claim 21 wherein the cationic anti-microbial agent and the malic acid are utilized in the form of a troche.*

*34. The improvement according to claim 21 wherein the cationic anti-microbial agent and the malic acid are utilized in the form of a lozenge.*

* * * * *